United States Patent
Lisby

(10) Patent No.: US 8,501,441 B2
(45) Date of Patent: Aug. 6, 2013

(54) TARGET AMPLIFICATION AND SEQUENCING WITH PRIMERS COMPRISING TRIPLEX FORMING MONOMER UNITS

(75) Inventor: Gorm Lisby, Veksø Sjælland (DK)

(73) Assignee: Quantibact A/S, Hvidovre (DK)

( * ) Notice: Subject to any disclaimer, the term of this patent is extended or adjusted under 35 U.S.C. 154(b) by 280 days.

(21) Appl. No.: 12/921,561

(22) PCT Filed: Mar. 10, 2009

(86) PCT No.: PCT/DK2009/050051
§ 371 (c)(1),
(2), (4) Date: Nov. 30, 2010

(87) PCT Pub. No.: WO2009/112032
PCT Pub. Date: Sep. 17, 2009

(65) Prior Publication Data
US 2011/0076728 A1 Mar. 31, 2011

(30) Foreign Application Priority Data
Mar. 10, 2008 (DK) .................. 2008 00366

(51) Int. Cl.
*C12Q 1/68* (2006.01)
*C12P 19/34* (2006.01)
*C07H 21/00* (2006.01)
(52) U.S. Cl.
USPC .......... 435/91.1; 435/6.1; 536/23.1; 536/24.3
(58) Field of Classification Search
USPC ............... 435/6.1, 91.1, 91.2; 536/23.1, 24.3
See application file for complete search history.

(56) References Cited

FOREIGN PATENT DOCUMENTS

WO    WO 2006/112818 A2    10/2006
WO    WO 2006/125447 A2    11/2006

OTHER PUBLICATIONS

Ulf B. Christensen et al., "Intercalating nucleic acids containing insertions of 1-0-(1-pyrenylmethyl)glycerol stabilisation of dsDNA and discrimination of DNA over RNA", Nucleic Acids Research, 2002, vol. 30, No. 22, pp. 4918-4925.

Igor A. Prokhorenko et al., "Phenylethynylpyrene-labeled oligonucleotide probes for excimer fluorescence SNP analysis of 23S rRNA gene in clarithromycin-resistant *Helicobacter pylori* strains", Mutation Research 599 (2006) 144-151.

Vyacheslav V. Filichev et al., "Stable and Selective Formation of Hoogsteen-Type Triplexes and Duplexes Using Twisted Intercalating Nucleic Acids (TINA) Prepared via Postsynthetic Sonogashira Solid-Phase Coupling Reactions", J. Am. Chem. Soc. 2005, 127, 14849-14858.

Vyacheslav V. Filichev et al., "1-, 2-, and 4-Ethynylpyrenes in the Structure of Twisted Intercalating Nucleic Acids: Structure, Thermal Stablility, and Fluorescence Relationship", Chem. Eur, J. 2008, 14, pp. 9968-9980.

Imrich Geci et al., "Synthesis of Twisted Intercalating Nucleic Acids Possessing Acridine Derivatives, Thermal Stability Studies", Bioconjugate Chem. 2006, 17, 950-957.

Amany M. A. Osman et al., "Using an aryl phenanthroimidazole moiety as a conjugated flexible intercalator to improve the hybridization efficiency of a triplex-forming oligonucleotide", Bioorganic & Medicinal Chemistry, 16 (2008) 9937-9949.

Manikandan Paramasivam et al., "Purine twisted-intercalating nucleic acids: a new class of anti-gene molecules resistant to potassium-induced aggregation", Nucleic Acids Research, 2008, vol. 36, No. 10, pp. 3494-3507.

International Search Report PCT/DK2009/050051 dated Jul. 31, 2009.

*Primary Examiner* — Jezia Riley
(74) *Attorney, Agent, or Firm* — Foley & Lardner LLP

(57) ABSTRACT

The current inventors have discovered that the incorporation of a triplex forming monomer unit into oligonucleotides surprisingly gives the oligonucleotide a number of favorable characteristics. The oligonucleotides are advantageous because they allow modulation of the melting temperature of an oligonucleotide, they have improved sequence specificity and they can form triplexes by Hoogsteen or reverse Hoogsteen base pairing with double stranded nucleic acids. Moreover, some of the oligonucleotides of the invention have useful fluorescent characteristics, and the oligonucleotides comprising a triplex forming monomer can be used as substrates for enzymatic manipulations such as primer extension.

31 Claims, 4 Drawing Sheets

TARGET AMPLIFICATION AND SEQUENCING WITH PRIMERS COMPRISING TRIPLEX FORMING MONOMER UNITS

SEQUENCE LISTING

The instant application contains a Sequence Listing which has been submitted in ASCII format via EFS-Web and is hereby incorporated by reference in its entirety. Said ASCII copy, created on Oct. 27, 2010, is named 30307407.txt and is 2,440 bytes in size.

BACKGROUND

Detection, target amplification and sequencing of nucleic acids are pivotal methods in molecular biology, in research as well as in clinical diagnostics, and key reagents in such methods are oligonucleotides acting as primers and/or probes.

Of main importance for primers and probes are their sequence specificity and also their affinity for a complementary nucleic acid. These features can be modulated by factors intrinsic to the oligonucleotide and factors extrinsic to the oligonucleotide. Intrinsic factors are e.g. the length and nucleic acid sequence composition of oligonucleotides. Also the uses of non-natural nucleotides or backbone modifications are intrinsic factors. However, the number of available non-natural nucleotides and backbone units are limited. Accordingly, there is a need for oligonucleotides with novel modifications that can be used in molecular biology methods.

Patent application WO 2006/125447 described a triplex forming monomer unit of the formula Z (described below) and demonstrated favorable characteristics of an oligonucleotide comprising a triplex forming monomer unit with regards to triplex formation with a double stranded nucleic acid. Based on the triplex forming characteristics, the inventors of the aforementioned patent application suggest using the oligonucleotide for detection, diagnosis and treatment. No details or data on such uses were provided.

Filichev at al., (Filichev V V, 2005) described the same triplex forming monomer unit as WO 2006/125447 and found stabilization of parallel duplex and parallel triplex by incorporation of the triplex forming monomer unit. Moreover, they found destabilization of Watson-Crick type RNA/DNA and DNA/DNA duplexes when triplex forming monomer units were inserted into an oligonucleotide, compared to the native oligonucleotide.

SUMMARY OF THE INVENTION

Figure 1:
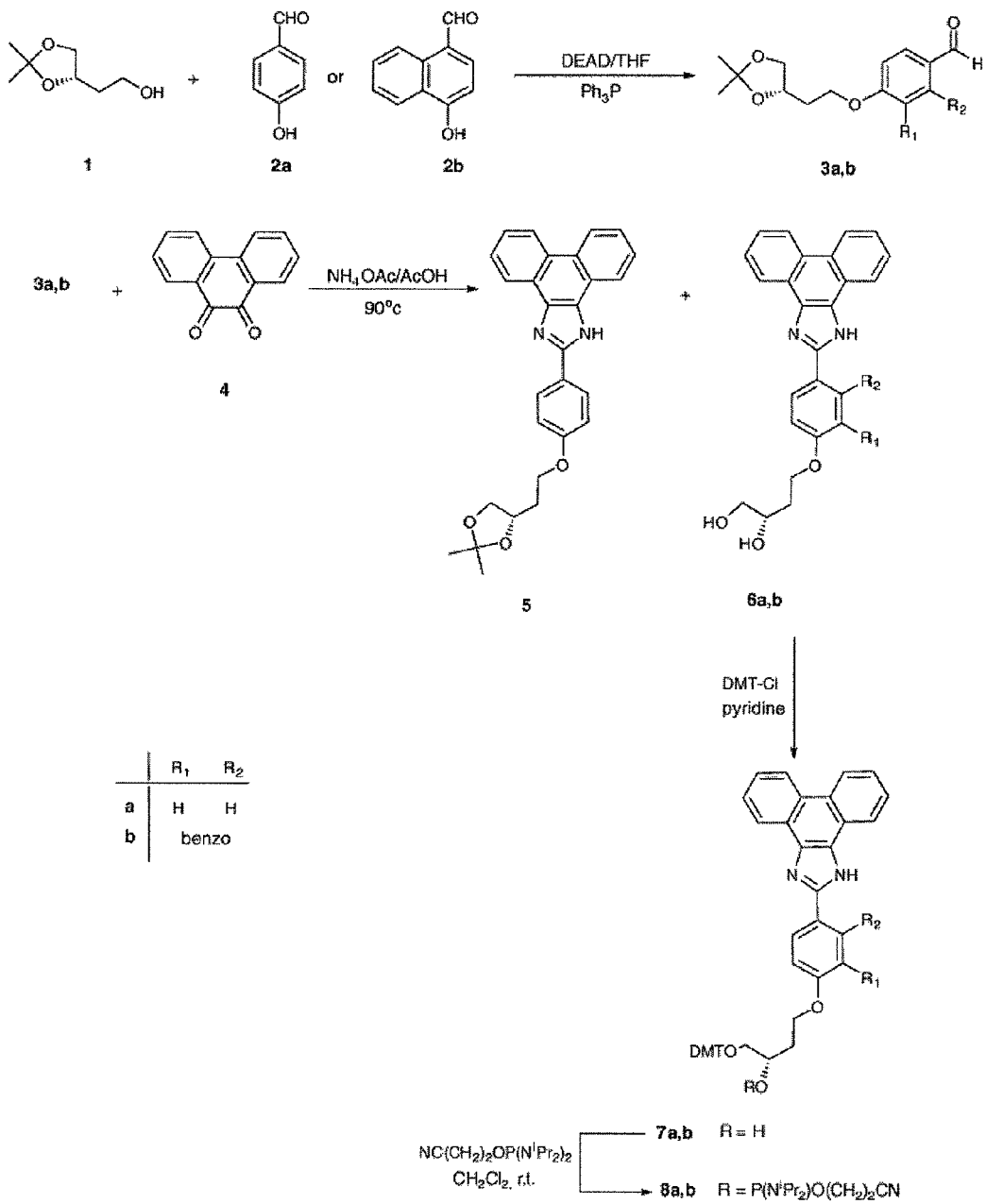
FIG. 1: The synthesis of intercalating nucleic acid monomers containing a 1H-phenanthro[9,10-d]imidazol-2-yl group.

The current inventors have discovered that the incorporation of a triplex forming monomer unit (herein also termed TINA monomer) into oligonucleotides surprisingly gives the oligonucleotide a number of favorable characteristics. Moreover, they have discovered that oligonucleotides comprising a triplex forming monomer can be used as substrates for enzymatic manipulations such as primer extension.

Thus, a first aspect of the present invention is an oligonucleotide of a length between 5 and 60 nt (nucleotides), comprising at least one TINA monomer unit of the formula Z, wherein said TINA monomer(s) is located at a position which is at least 1 monomer from the 3' end of the oligonucleotide.

Such oligonucleotide can be used in various molecular biological methods.

Thus, a second aspect of the invention is a method of comprising the steps of
a. Providing a template nucleic acid
b. Providing a first primer
c. Providing a polymerase
d. Providing nucleotide triphosphates
e. Mixing the components of steps a-d and providing conditions, that allow the primer to anneal to the template wherein the primer is preferably an oligonucleotide of the invention.

The steps may be part of a molecular biology technique, such as a sequencing reaction, a transcription reaction or a nucleic acid target amplification method (NAT)—such as polymerase chain reaction (PCR), Nucleic Acid Sequence Based Amplification (NASBA), Transcription Mediated Amplification (TMA), Strand Displacement Amplification (SDA) or Ligase Chain Reaction (LCR). If the steps are part of a NAT reaction, the NAT reaction may be performed simply to amplify a target region of the template nucleic acid. Alternatively, the NAT may be performed quantitatively to determine the amount of a target region of the template nucleic acid. A quantitative NAT (e.g. PCR) reaction may comprise detection probes that may be oligonucleotides of the invention.

The oligonucleotides of the invention are advantageous because they allow modulation of the melting temperature of an oligonucleotide, they have improved sequence specificity and they can form triplexes by Hoogsteen or reverse Hoogsteen base pairing with double stranded nucleic acids. Moreover, some embodiments of the oligonucleotides of the invention have useful fluorescent characteristics.

DISCLOSURE OF THE INVENTION

Oligonucleotide of the Invention

In a first aspect, the present invention provides an oligonucleotide of a length between 5 and 60 nt. comprising a TINA monomer of the formula Z, wherein said TINA monomer is located at a position which is at least 1 monomer from the 3' end of the oligonucleotide.

Even more preferred is a length between 8 and 50 nt. and most preferred is a length between 10 and 40 nt.

Triplex forming monomer unit, Z

Z can be described by general structure:

wherein X is a backbone monomer unit that can be incorporated into the backbone of a oligonucleotide or a oligonucleotide analogue, or PNA, or PNA analogues, L is a linker, $I_1$ is a first intercalator comprising at least one essentially flat conjugated system, which is capable of co-stacking with nucleobases of DNA, RNA or analogues thereof, C is an optional conjugator and $I_2$ is a second intercalator comprising at least one essentially flat conjugated system, which is capable of co-stacking with nucleobases of DNA, RNA or analogues thereof.

A flexible basestacking monomer (Z) comprise at least two intercalating systems $I_1$ and $I_2$ which are linked by a conjugator C which provides the necessary structural rigidity and twisting flexibility. The latter is believed to be important to help intercalators to adjust themselves to an appropriate position inside the nucleic acid helix.

In a preferred embodiment, the backbone X is capable of being incorporated into a oligonucleotide of DNA, RNA, HNA, MNA, ANA, LNA, CAN, INA, CeNA, TNA, (2'-NH)-TNA, (3'-NH)-TNA, α-L-Ribo-LNA, α-L-Xylo-LNA, β-D-Ribo-LNA, β-D-Xylo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3.0]amide-DNA, 3-D-Ribopyranosyl-NA, α-L-Lyxopyranosyl-NA, 2'-R-RNA, 2'-OR-RNA, 2'-AE-RNA, α-L-RNA, β-D-RNA, and combinations and modifications thereof.

In another embodiment, the backbone monomer unit X comprises alkylendiol, such as ethyleneglycol or 1-O-methyleneglycerol which optionally has the alkylenediol partly comprised in a ring system, such as glycon. For example, the backbone monomer X may be a part of four, five or six member rings which eventually have heteroatoms selected from nitrogen, sulphur, phosphorous, and oxygen. Preferably, the alkylenediol directly links neighbouring monomer units of the oligonucleotide, and it is to be understood that in this embodiment, the alkylenediol may still be part of a ring system such as e.g. glycon.

In one embodiment, the linker L of the flexible basestacking monomer comprises 0-60 atoms.

In another embodiment, L comprises a chain or a ring or combinations thereof and/or substitutions thereof.

In still another embodiment, L comprises an alkyl chain or an oxaalkyl chain or an azaalkyl chain or a thiaalkyl chain or an carboxamide group or an thiocarboxamide group or an sulphonamide group or combinations thereof.

The combination of X and L provides a system which places intercalating system of $I_1$-C-$I_2$ in the core of nucleic acid helixes with ability to stack with nucleic acid bases.

$I_1$ of the flexible basestacking monomer is a first intercalator comprising at least one essentially flat conjugated system, which is capable of co-stacking with nucleobases of DNA, RNA or analogues thereof.

In an embodiment, $I_1$ is a monocyclic or polycyclic aromatic ringsystem optionally selected from the group of a benzene, naphthalene, azulene, bicyclic heteroaromatic ring systems and substitutions thereof.

In a preferred embodiment, $I_1$ is positioned with L and C in position 1,2 of the monocyclic or polycyclic aromatic ringsystem.

In yet another embodiment, $I_1$ is positioned with L and C in position 1,3 of the monocyclic or polycyclic aromatic ringsystem, In another embodiment, $I_1$ is positioned with L and C in position 1,4 of the monocyclic or polycyclic aromatic ringsystem, In a more preferred embodiment is $I_1$ a benzene ring with L and C in an ortho- or para-position.

C of the flexible basestacking monomer is an optional conjugator. In a preferred embodiment where C is non-optional, C is selected from the group of an alkyl of from 1 to 12 carbons, alkenyl of from 2 to 12 carbons, alkynyl 2 to 25 carbons or diazo or combinations thereof with a length of no more than 25 carbons or/and nitrogen atoms.

In an alternative embodiment the flexible basestacking monomer does not contain any conjugator. Thus, $I_1$ and $I_2$ may be linked directly e.g. via a conjugated system.

In another embodiment, C is selected from the group consisting of straight-chain or branched-chain or monocyclic aromatic rings and substitutions thereof which eventually have heteroatoms selected from nitrogen, sulphur, phosphorous, and oxygen.

In still another embodiment, the alkenyl of C is an acetylene or repetitive acetylenes.

In a preferred embodiment, the unit length of the backbone monomer unit X including a phosphorous atom is less than 6 atoms, wherein the backbone unit length is the shortest distance from one monomer to the next.

In a preferred embodiment, the linking moiety L has a length of at least 2 atoms and eventually possesses heteroatoms selected from nitrogen, sulphur, phosphorous, and oxygen. Preferably, the linking moiety L has a length between 2 and 10 atoms, more between 2 and 5 atoms. In a most preferred embodiment, the linking moiety has a length of 3 atoms corresponding to 5 bonds between X and $I_1$.

$I_2$ of the flexible basestacking monomer is a second intercalator comprising at least one essentially flat conjugated system, which is capable of co-stacking with nucleobases of DNA, RNA or analogues thereof.

In a preferred embodiment, $I_2$ is selected from the group of bi-cyclic aromatic ringsystems, tricyclic aromatic ringsystems, tetracyclic aromatic ringsystems, pentacyclic aromatic ringsystems and heteroaromatic analogues thereof and substitutions thereof.

Figure 4:
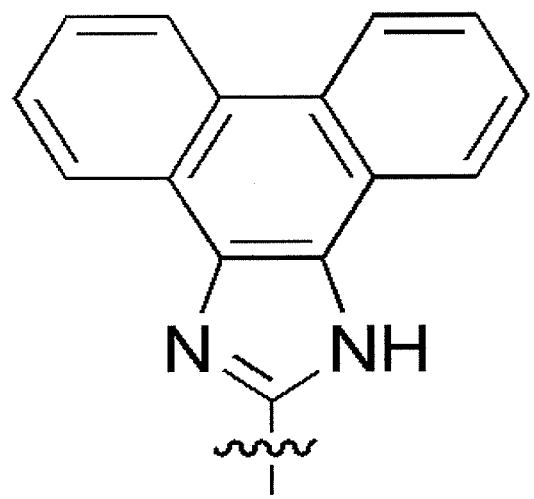
FIG. 4: A 1H-phenanthro[9,10-d]imidazol-2-yl group.

In a particular embodiment $I_2$ is a 1H-phenanthro[9,10-d]imidazol-2-yl group or pyrene (FIG. 4).

In a preferred embodiment, the flexible basestacking monomer is part of a oligonucleotide or oligonucleotide analogue.

In another preferred embodiment, the flexible basestacking monomer is adapted for incorporation into a oligonucleotide.

In a preferred embodiment, the flexible basestacking monomer adapted for incorporation into a oligonucleotide is selected from the group of a phosphoroamidite, a phosphordiamidite, a phosphordiester, a phosphortriester, a phosphonate, a H-phosphonate, a phosphite, a chlorophosphite, a chlorophosphoramidite, a phosphonamidite, a phosphonchloridite, a triphosphate, a diphosphate.

In a most preferred embodiment, the flexible basestacking monomer (Z) can be described by the formula:

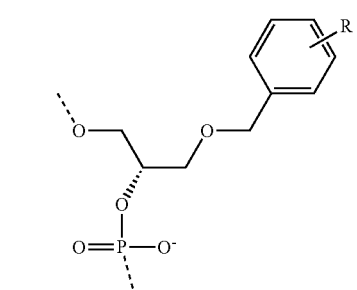

wherein R is selected from the group of arylethynyl, pyreneethynyl, and 1H-phenanthro[9,10-d]imidazol-2-yl group R may be substituted in the ortho, meta or para position of benzene. More preferred are the ortho and para positions.

Oligonucleotide Embodiments

The oligonucleotide of the invention has a variety of surprising and beneficial applications, as will be clear from other aspects of the invention and from the examples. A main use of such an oligonucleotide is for primer extension in molecular biology techniques such as nucleic acid target amplification (e.g. PCR) or nucleic acid sequencing.

In a preferred embodiment, the oligonucleotide comprises a number of TINA monomers selected from the group consisting of 1, 2, 3, 4, 5, 6, and 7 and, wherein said TINA monomers are located at a position which is at least 1 monomer from the 3' end of the oligonucleotide. I.e. the first monomer of the oligonucleotide is not a TINA monomer.

Preferably, the TINA monomers are not placed adjacent to each other, i.e. they are separated by at least one nucleotide monomer of the oligonucleotide. Even more preferred is a separation of 2 or 3 nucleotide monomer units. More preferred is a separation of 5 or 6 or 10, 11 or 12 corresponding to respectively a ½ helical turn or 1 helical turn.

Since a polymerase typically senses the characteristics of the primer annealed to the template, the TINA monomer is preferably located at least 1 monomer from the 3' end of the oligonucleotide. Otherwise, the polymerase will not accept the oligonucleotide as a primer. The allowable position may vary from polymerase to polymerase.

Thus, in a preferred embodiment, the TINA monomers are located at a position selected from the group consisting of at least 2 monomers from the 3' end of the oligonucleotide, at least 3 monomers from the 3' end of the oligonucleotide, at least 4 monomers from the 3' end of the oligonucleotide, at least 5 monomers from the 3' end of the oligonucleotide, at least 6 monomers from the 3' end of the oligonucleotide, at least 7 monomers from the 3' end of the oligonucleotide, at least 8 monomers from the 3' end of the oligonucleotide, at least 9 monomers from the 3' end of the oligonucleotide at least 10 monomers from the 3' end of the oligonucleotide, at least 11 monomers from the 3' end of the oligonucleotide, at least 12 monomers from the 3' end of the oligonucleotide, at least 13 monomers from the 3' end of the oligonucleotide, at least 14 monomers from the 3' end of the oligonucleotide and at least 15 monomers from the 3' end of the oligonucleotide.

Most preferred is a position at least 6 monomers from the 3' end of the oligonucleotide.

In another embodiment, the TINA monomer units are located at a position which is no more than 5 monomers from the 5' end of the oligonucleotide, such as 4, 3, 2 and 1 monomers from the 5' end of the oligonucleotide. In one embodiment, the TINA monomer is located at the 5' end of the oligonucleotide.

Preferably, the oligonucleotide of the invention further comprises monomer units selected from the group consisting of DNA units, RNA units, LNA units and 2'-OH-modified units. As will be understood, the term monomer unit is used for the repeating units of an oligonucleotide, i.e. typically nucleotides. A monomer unit may also be a PNA monomer (peptide nucleic acid monomer).

Incorporation of non-natural monomer units such as LNA monomers, PNA monomers or 2-OH-modified units may be desired to increase the melting temperature of the oligonucleotide hybridized to a complementary template strand. Some monomer units may also be used to decrease the melting temperature of the oligonucleotide hybridized to a complementary template strand. If the oligonucleotide is to be used in cell extracts, modified monomer units may also be used to prevent or reduce enzymatic degradation of the oligonucleotide.

In a preferred embodiment, the oligonucleotide of the invention does not comprise any unmodified RNA monomer units. The presence of RNA monomer units in an oligonucleotide will often decrease the stability, i.e. make the oligonucleotide more prone to nucleolytic degradation.

In one embodiment, the oligonucleotide of the invention comprises a contiguous stretch of 3 deoxynucleotides at the 3' end to ensure proper initiation of the polymerization. This is desired because some DNA and RNA polymerases have a requirement for DNA monomers at the 3' region end of the primer. Most polymerases, however, do not have this requirement.

The oligonucleotide of the invention may comprise a restriction site. A restriction is a sequence that enables a restriction enzyme to cleave the oligonucleotide. Typically, the restriction sequence is palindromic and typically, the restriction enzyme cleaves double stranded nucleic acids, wherefore the oligonucleotide should be base paired to a complementary oligonucleotide for restriction digestion. Some restriction enzymes can also digest single stranded nucleic acids. Exemplary restriction enzymes are EcoRI, BamHI and XhoI. When the oligonucleotide of the invention is used for polymerase chain reaction (PCR), restriction sites may be incorporated into the oligonucleotide of the invention to facilitate cloning of the PCR-product. The restriction site will normally be present at the 5' end of the oligonucleotide.

Labels

The oligonucleotide of the invention may comprise a reporter dye. Preferably, the reporter dye is selected from the group consisting of FAM™, TET™, JOE™, VIC™, SYBR® Green, 6 FAM, HEX, TET, TAMRA, JOE, ROX, Fluorescein, Cy3, Cy5, Cy5.5, Texas Red, Rhodamine, Rhodamine Green, Rhodamine Red, 6-CarboxyRhodamine 6G, Alexa Fluor, Oregon Green 488, Oregon Green 500 and Oregon Green 514.

Preferably, the oligonucleotide also comprises a quenching dye. In a preferred embodiment, the quenching dye is selected from the group consisting of TAMRA™, Black Hole Quencher™, DABCYL, BHQ-1, BHQ-2, DDQ I, DDQ II and Eclipse Dark Quencher.

The use of reporter and quenching dye is desirable because it allows various kinds of quantifications, both when the oligonucleotide of the invention is used as a primer and when the oligonucleotide of the invention is used a detection probe during or after the NAT process.

Typically, the reporter dye and the quencher dye are located near each other in the oligonucleotide of invention, allowing laser-induced fluorescence emitted by the reporter to be quenched by the quencher dye. When the oligonucleotide binds to a complementary template strand, the reporter dye and the quencher dye are separated from each other such that the quencher no longer quenches the signal from the reporter.

Thus, in one embodiment, the oligonucleotide is capable of forming a stem-loop structure, wherein the quencher and reporter dye are brought into proximity in the stem. In one embodiment, the oligonucleotide is a so-called molecular beacon. The quencher and the reporter are no longer in proximity, when the molecular beacon base pairs to a template strand. Therefore the laser-induced signal from the reporter dye is no longer quenched. In another embodiment, the oligonucleotide is a so-called scorpion primer. The scorpion primer comprises a stem-loop that refolds when the primer is extended. Thereby, the reporter dye and the quencher dye are no longer in close proximity and the signal from the reporter dye is no longer quenched.

In an alternative embodiment, the reporter dye and the quencher dye is present on two different oligonucleotides. In this embodiment, the reporter and the quencher dye is brought into proximity when the two oligonucleotides base pairs to adjacent sites on a template strand. Preferably, the two oligonucleotides are separated by no more than 3 nucleotides.

In yet another embodiment, the oligonucleotide is a so-called taqman probe. The taqman probe is complementary to the region between the two primer binding sites of the template nucleic acid and therefore base pairs to this region. When a polymerase extends a primer it will encounter the taqman probe and by way of its 5-3' exonuclease activity, it will digest the taqman probe. Thereby, the reporter and quencher dye of the taqman probe are separated from each other.

Instead of using a reporter dye and a quencher dye, a so-called FRET (fluorescence resonance energy transfer) pair comprising a donor fluorophor and an acceptor fluorophor may be used. When the donor fluorophor is excited by an external light source, it emits light at a wavelength, which excites the acceptor fluorophor, which in turn emits light at a different wavelength, which can be detected and measured. The energy is only transferred from the donor to the acceptor if the donor fluorophor and acceptor fluorophor are in close proximity.

Preferred FRET pairs include BFP-YFP, CFP-YFP, GFP-DsRed, GFP-Cy3, GFP-mOrange, YFP-RFP, FAM-ROX, FAM-Cy5, FAM-Hex, FAM-TAMRA and Cy3-Cy5.

In yet another embodiment, the oligonucleotide of the invention comprise a RNA promoter sequence such as a T7 RNA polymerase promoter sequence, T3 RNA polymerase promoter sequence or a SP6 RNA polymerase promoter sequence. Such oligonucleotide is of interest because it can be hybridized to the complementary template strand and direct RNA polymerase mediated RNA transcription of the template strand. Thus, the oligonucleotide can be used for transcription mediated amplification (TMA).

Method of the Invention

A second aspect of the invention is a method comprising the steps of
  a. Providing a template nucleic acid
  b. Providing a first primer
  c. Providing a polymerase
  d. Providing nucleotide triphosphates
  e. Mixing the components of steps a-d and providing conditions, that allow the primer to anneal to the template Preferably, the first primer is an oligonucleotide as described in the embodiments of the first aspect. As will be clear, various embodiments of the method of the second aspect will or may require different embodiments of the oligonucleotides described in the first aspect.

In a preferred embodiment, the method further comprises a step of:
  f. Under conditions allowing primer extension, extending the first primer annealed to the template.

In an alternative embodiment described in more detail below, the primer is not extended. Instead the primer base paired to the template nucleic acid enables RNA transcription. Thus, the primer comprises a RNA polymerase promoter sequence.

Nucleic Acid Sequencing

In a preferred embodiment, the primer is fluorescently labeled.

In another embodiment, a fraction of the nucleotide triphosphates consists of dideoxynucleotide triphosphates. In a preferred embodiment, the included dideoxynucleotide triphosphates are fluorescently labeled, preferably with different fluorescent labels. As the skilled person will recognize, the use of a fluorescent primer or fluorescently labeled dideoxynucleotides are useful for nucleic acid sequencing.

In a related embodiment, neither primer nor dideoxynucleotides are fluorescently labeled, as such labeling is unnecessary for pyrosequencing.

Target Amplification

In a preferred embodiment, the method further comprises the steps of
  g. Providing a second primer, which is complementary to the first extension product of step f
  h. Denaturing the product of the step f
  i. Under conditions allowing primer extension, extending the second primer annealed to the first extension product Thus, steps g-i may be referred to as second strand synthesis.

In one embodiment, the template nucleic acid is RNA, wherefore the polymerase is a reverse transcriptase.

In a preferred embodiment, the second primer is an oligonucleotide of the invention and in yet another embodiment, both the first and the second primer is an oligonucleotide of the invention.

If the steps of denaturation, annealing and extension are repeated, such cycles enable amplification of the target sequence and will be recognized as PCR (polymerase chain reaction).

Preferably, at least 10 repetitions of denaturation, annealing and extension are performed. Typically, 30-45 cycles are carried out.

When cycling the temperature, it is important that the polymerase is thermo stable. Otherwise, polymerase will have to be added after each denaturation step.

Transcription Mediated Amplification (TMA)

As mentioned, one embodiment of the invention involves transcription. Thus, the first or the second primer comprises a RNA promoter sequence that enables transcription. The template nucleic acid may be either DNA or RNA. If the template is RNA, a reverse transcriptase will be used for first strand synthesis. After first strand synthesis, second strand synthesis may be done to generate a double stranded promoter sequence. Alternatively, a double stranded promoter sequence may be generated by adding an oligonucleotide complementary to the RNA promoter sequence of the first primer.

Strand Displacement Amplification (SDA)

In a preferred embodiment, the NAT process is an isothermal strand displacement amplification reaction. In this embodiment, the method comprises a third and a fourth primer and also a restriction enzyme. The third and the fourth primers are so-called bumper primers that are used to displace the extension products of the inner primers (the first and the second primers). When the extension products of the inner primers are displaced from template strand, they can bind another (inner) primer for extension. When this primer has been extended, one strand of the double stranded product is nicked by the restriction enzyme. Nicking is made possible, because the inner primers comprise a restriction site. However, only one of the strands will be cleaved—either because of the presence of a modification in the primer—or because the extension product contains modified nucleotides (e.g. dCTPαS) that only will allow the restriction enzyme to cleave the original primer (that contains unmodified nucleotides). The modification may e.g. be the presence of a phosphorothioate bond. In this way, exponential isothermal nucleic acid amplification is enabled. 1, 2, 3 or 4 of the primers may be oligonucleotides of the invention.

In a preferred embodiment, all four primers are oligonucleotides of the invention.

Ligase Chain Reaction (LCR)

Ligase Chain Reaction (LCR) is a method of DNA amplification similar to PCR. LCR differs from PCR because it amplifies the probe molecule rather than producing amplicon through polymerization of nucleotides. Two probes are used per each DNA strand and are ligated together to form a single probe. LCR uses both a DNA polymerase enzyme and a DNA ligase enzyme to drive the reaction. Like PCR, LCR requires a thermal cycler to drive the reaction and each cycle results in a doubling of the target nucleic acid molecule. LCR can have greater specificity than PCR.

The term LCR covers both conventional LCR, gap LCR, asymmetric gap LCR and variations hereof.

In an embodiment at least one of the one of the LCR probes per DNA strand are oligonucleotides of the invention.

In a particular embodiment of invention, four LCR probes are oligonucleotides of the invention.

Quantitative PCR

It is an object of the present invention to provide methods of performing quantitative PCR (qPCR). Thus, in one embodiment, the reaction mixture further comprises a detection probe comprising a sequence which is complementary to a region between the first and the second primer binding site of the first or the second extension product or to the first or the second primer binding site.

In a preferred embodiment, the probe is a dual labeled probe that will be digested by the 5'-3' exonucleolytic activity of the polymerase. Such probe is often referred to as a Taqman probe. As described above, the labels of the probe are typically a reporter dye and a quencher dye. Thus, the quencher dye quenches the signal from the reporter dye if both labels are present on the same probe. If the probe is digested, the signal from the reporter dye will no longer be quenched. Therefore, the signal from the reporter dye will correlate to the amount of template strand in the reaction. I.e. the signal can be used to follow the course of the amplification reaction.

In another embodiment, the probe is capable of forming a stem-loop structure. As also described above, a reporter dye and a quencher dye may be located in the stem such that the quencher quenches the signal from the reporter dye. When the probe base pairs to a template strand, the reporter dye and quencher dye are separated, wherefore the signal from the reporter dye is no longer quenched. Such probes are often referred to as molecular beacons.

A related type of probe is the so-called scorpion probes. These probes actually function as primers and they refold when they are extended and thereby the quencher dye is separated from the reporter dye. Thus, the first or the second primer of the method of the invention may be a scorpion probe to facilitate qPCR.

As an alternative to having the template strand causing the reporter dye and the quencher dye of a probe to separate, the template strand may also cause them to get into proximity. In such an embodiment, the labels can be located on two separate probes. Thus, in a preferred embodiment, the reaction mixture further comprises a second probe that is complementary to a region between the first and the second primer binding site of the first or the second extension product, and wherein the first and the second probe will base pair to adjacent sites, thereby bringing the 3' end of one probe into proximity with the 5' end of the other probe.

As mentioned above, instead of using a reporter dye and a quencher dye, a so-called FRET (fluorescence resonance energy transfer) pair comprising a donor fluorophor and an acceptor fluorophor may be used.

Any of the above mentioned detection probes might be an oligonucleotide of the invention and hence comprise a Z unit.

Instead of using a probe to detect the product of the PCR reaction, a double stranded specific reporter dye may be used. Hence, in a preferred embodiment, the reaction mixture further comprises double stranded specific reporter dyes such as SYBR green I, SYBR green II and SYBR Gold.

Triplex Detection Probe

In a preferred embodiment, the reaction mixture further comprises a triplex forming probe (TFO) that can form a triplex with the extension product (e.g. PCR product). If the triplex forming probe comprises a Z monomer unit, triplex formation may be directly measured by laser/external light source-excited light emission.

However, any of the above reporter dye systems including FRET pairs may be used in connection with a triplex forming detection probe. Thus, in a preferred embodiment, the triplex forming probe is capable of forming a stem-loop structure in analogy with a molecular beacon.

Also in analogy with the detection probes described above, the reaction mixture may comprise a second triplex forming probe, which forms a triplex adjacent to the triplex formed with the first triplex probe. Preferably the first and second triplex forming probe comprises a reporter dye and a quencher dye respectively. Alternatively, they preferably comprise a FRET pair.

The two triplex forming probes may be joined by a linker such as a C18 linker, a PEG linker, a C9, a C7, a C6, a cyclohexan, a cyclooctan, a ethyleneoxide or any combination hereof.

In another embodiment, the triplex formation is achieved by two separate oligonucleotide detection probes and the single-stranded extension product: One oligonucleotide detection probe forms an antiparallel duplex with the single-stranded extension product from either the first or the second primer and a second oligonucleotide detection probe forms a parallel triplex with the antiparallel duplex consisting of the single-stranded extension product and the first oligonucleotide detection probe.

In yet another embodiment, the TFO is designed as: O1-L-O2, where O1 and O2 are oligonucleotides and L is a linker (e.g. as described above) between O1 and O2. O1 forms an antiparallel duplex with the single-stranded extension product from either the first or the second primer and O2 folds back on the antiparallel duplex to form a parallel triplex.

In yet another embodiment, the TFO forms a parallel triplex with the double-stranded extension product.

Any of the above mentioned detection probes may be an oligonucleotide of the invention and hence comprise a TINA monomer of the formula Z for improved sequence specificity or increased melting temperature of the detection probe base paired to a complementary sequence. In one embodiment, the TINA monomer may be used to decrease the melting temperature of the detection probe.

When the detection probe is a triplex forming probe, it is preferred that it comprises a contiguous stretch of at least 3 pyrimidines and preferably no more than 15 pyrimidines. In another preferred embodiment, the detection probe comprises a contiguous stretch of at least 3 purines and preferably no more than 15 purines.

Triplex Stabilization of Primer Annealing

In a preferred embodiment relating to NAT, the reaction further comprises a triplex forming oligonucleotide that can form a triplex with the first primer base paired to a template strand or with the second primer base paired to a template strand.

Thus, the triplex forming oligonucleotide will stabilize base pairing between the primer and the template.

In a preferred embodiment, the 3' end of the primer has a number of nucleotides that are not engaged in triplex formation, said number being selected from the group consisting of at least 5 nucleotides, at least 7 nucleotides, at least 10 nucleotides, at least 13 nucleotides and at least 16 nucleotides.

In another preferred embodiment, the number of nucleotides that are not engaged in triplex formation is at least 3 and no more than 25 nt, preferably at least 5 and no more than 20 nt, more preferably at least 7 and no more than 18 nt.

As an alternative to using a primer and a TFO, both functionalities may be included in the same oligonucleotide. Thus, a first part of the oligonucleotide forms an antiparallel duplex with the template nucleic acid and a second part of the oligonucleotide folds to form a triplex. Preferably, the first part of the oligonucleotide comprises the 3' end of the oligonucleotide. This oligonucleotide may have the formula: O1-L-O2, where O1 and O2 are oligonucleotides and L is a linker between O1 and O2.

REFERENCES

Filichev V V, P. E. (2005). Stable and selective formation of hoogsteen-type triplexes and duplexes using twisted intercalating nucleic acids (TINA) prepared via postsynthetic Sonogashira solid-phase coupling reactions. *J Am Chem Soc*, October 26; 127(42):14849-58.

Osman A. M. A. et al. Using an aryl phenanthroimidazole moiety as a conjugated flexible intercalator to improve the hybridization efficiency of a triplex-forming oligonucleotide. Bioorg Med. Chem. 2008 Dec. 1; 16(23):9937-47. Epub 2008 Oct. 17.

Filichev V V. et al. 1-, 2-, and 4-ethynylpyrenes in the structure of twisted intercalating nucleic acids: structure, thermal stability, and fluorescence relationship. Chemistry. 2008; 14(32):9968-80.

Géci I et al. Synthesis of twisted intercalating nucleic acids possessing acridine derivatives. Thermal stability studies. Bioconjug Chem. 2006 July-August; 17(4):950-7.

EXAMPLES

Example 1

Twisted Intercalating Nucleic Acids (TINA) surprisingly increases Ta and ΔTa in PCR Introduction:

Twisted Intercalating Nucleic Acids (TINA) is an intercalator designed to stabilize Hoogsteen triplex DNA, but surprisingly also under special conditions can stabilize Watson-Crick antiparallel duplexes formations. Although not expected, it was planned to investigate if TINA-DNA primers will be able to increase the annealing temperature (Ta) and delta Ta (ΔTa) of any PCR reaction or variation hereof (e.g. classical ("end-point") qualitative PCR/RT-PCR, classical ("end-point") quantitative PCR/RT-PCR, real-time qualitative PCR/RT-PCR, real-time quantitative PCR/RT-PCR). The effect of this increase in Ta and ΔTa will be two-fold: An increase in Ta will by itself reduce the general probability of a PCR primer to anneal unspecific, and the increase in ΔTa will likewise reduce the probability of unspecific binding. This increase in specific primer annealing can be utilized to increase the overall specificity of a given assay. Alternatively, by "relaxing" the stringency of the primer annealing, an increased sensitivity can be achieved without compromising specificity compared to an identical assay without TINA-DNA. Likewise, regarding the internal probe in real-time PCR reactions, an increase in Ta will by itself reduce the general probability of a PCR probe to anneal unspecific, and the increase in ΔTa will likewise reduce the probability of unspecific binding.

Material and Methods:

Antiparallel Duplex DNA/TINA-DNA Primer PCR:

As a model PCR system, the internal positive control system at the Section for Molecular Biology. Department of Clinical Microbiology, Hvidovre Hospital, Copenhagen Denmark was chosen. Nucleic acid from the seal alpha herpesvirus, phocid herpesvirus type 1 (PhHV-1) was extracted as follows: 200 ul virus culture suspension was purified using the "Total NA Serum_Plasma_Blood" protocol on a MagNA Pure LC instrument (Roche, cat. no. 12236931001) in combination with the MagNA Pure LC Total Nucleic Acid Isolation Kit (Roche, cat. no. 03038505001) according to the instructions of the manufacturer. (Briefly, the sample material is placed into the wells of the Sample Cartridge-Lysis/Binding Buffer is added to the sample, resulting in complete cell lysis and release of nucleic acids—nucleases are denatured—proteinase K is added to the samples and proteins are digested—nucleic acids bind to the silica surface of the added MGPs due to the chaotropic salt conditions, isopropanol, and the high ionic strength of the Lysis/Binding Buffer—MGPs with bound nucleic acids are magnetically separated from the residual lysed sample—MGPs with bound nucleic acids are washed repeatedly with Wash Buffer to remove unbound substances like proteins (nucleases), cell membranes, PCR inhibitors such as heparin or hemoglobin, and to reduce the chaotropic salt concentration—again MGPs with bound total nucleic acid are magnetically separated from the Wash Buffer containing residual sample debris—the purified nucleic acids are eluted at 70° C. from the MGPs in the wells of the Elution Cartridge, whereas the MGPs are retained in the reaction tip and discarded). Purified nucleic acid was eluted in a 100 μl volume corresponding to a concentration of approximately 300,000 virus copies/ml.

1. DNA-PCR: First, an optimization was performed using 3,000 copies of PhHV-1 and different concentrations of the two primers (Primer 1: 5' GGGCGAATCACAGATTGAATCT 3' (SEQ ID NO: 1), Primer 2: 5' GCGGTTCCAAACGTACCAA 3', (SEQ ID NO: 2)), MgCl$_2$, and TAQ polymerase. Following choice of optimal PCR variables, the maximum annealing temperature (Ta) was identified using a Eppendorf MasterCycler gradient thermocycler with the following PCR parameters: 42 cycles of 94° C. for 30 sec, 60-72° C. gradient for 2 min, and subsequent visualization by electrophoresis of 7.5 μl of the 50 μl PCR product on an 4% agarose gel at 3 V/cm for 30 min. Subsequently, single point mutation primers were constructed (MutPrimer 1: 5' GGGCGAATCACAGATTGAGTCT 3', (SEQ ID NO: 3), MutPrimer 2: 5' GCGGTTCCAAACGTATCAA 3', (SEQ ID NO: 4), bold=mutation) and ΔTa for the mutation was determined.

2. TINA-PCR: Using PCR conditions optimal for classical DNA-PCR as described above, the maximum Ta was determined for 5' TINA-DNA primers (TINA modified Primer 1: 5' XGGGCGAATCACAGATTGAATCT 3', (SEQ ID NO: 5), TINA modified Primer 2: 5' XGCGGTTCCAAACGTAC-CAA 3', (SEQ ID NO: 6), -X=TINA). Subsequently, single point mutation primers were constructed (TINA modified MutPrimer 1: 5' XGGGCGAATCACAGATTGAGTCT 3', (SEQ ID NO: 7), TINA modified MutPrimer 2: 5' XGCGGT-TCCAAACGTATCAA 3', (SEQ ID NO: 8), -X=TINA, bold=mutation) and ΔTa for the mutation was determined.
Results:
Optimal PCR Conditions:
By intensity on agarose gel electrophoresis, the following combination of variables was chosen for the PhHV-1 PCR reaction in a 50 µl reaction volume: 1× TaqMan Buffer A (Applied Biosystems), 3.5 mM $MgCl_2$, 200 µM dNTP each, 1 U/50 µl AmpliTaq Gold (Applied Biosystems)
Ta and ΔTa:
Antiparallel duplex PCR: The maximum Ta for the DNA-primers was 66.5° C., and ΔTa for the mutation was 1.6° C. The maximum Ta for the TINA-DNA-primers was 71.6° C., and ΔTa for the mutation was 3.5° C.
Conclusion:
Antiparallel duplex PCR: The incorporation of TINA increased the maximum Ta with 5.1° C. (from 66.5° C. to 71.6° C.) and ΔTa for the single mutation was increased with 1.9° C. (from 1.6° C. to 3.5° C.).

Example 2

Synthesis of Intercalating Nucleic Acid Monomers Containing a 1H-phenanthro[9,10-d]imidazol-2-yl Group The synthetic route toward the intercalating nucleic acid monomers (6a,b) is shown in FIG. 1. The key intermediates 3a,b were synthesized from (S)-2-(2,2-dimethyl-1,3-diox-olan-4-yl)ethanol (1) by reaction with 4-hydroxybenzaldehyde (2a) or 4-hydroxy-1-naphthaldehyde (2b) under Mitsunobu conditions32 (DEAD, THF, and Ph3P) in high yields 81% and 92%, respectively (FIG. 1). Subsequent treatment of 3a,b with phenanthrene-9,10-dione (4) and ammonium acetate in hot glacial acetic acid afforded the monomers 6a,b. When starting from 3a the product mixture was separated by silica gel column chromatography to afford the deprotected (S)-4-(4-(1H-phenanthro[9,10-d]imidazol-2-yl)phenoxy) butane-1,2-diol (6a) in 72% yield and a minor amount of the corresponding diol (5) still protected with an isopropylidene group. Due to exchange of the imidazole protons, a line broadening was observed in the $^1$H NMR spectrum of (5). This resulted in a broad singlet for the neighboring protons in the phenanthrene ring at C-4 and C-11. The corresponding compound (S)-4-(4-(1H-phenanthro[9,10-d]imidazol-2-yl) naphthalen-1-yloxy)butane-1,2-diol (6b) was isolated fully deprotected by precipitation in 80% yield without chromatographic purification. The primary hydroxy group of compounds (6a,b) was protected by reaction with 4,4'-dimethoxytrityl chloride (DMT-Cl) in anhydrous pyridine at room temperature under a N2 atmosphere. Silica gel purification afforded the DMT-protected compounds 7a,b in 79% and 56% yield, respectively. The secondary hydroxy group of these compounds was phosphitylated overnight with 2-cyanoethyl N,N,N',N'-tetraisopropyl phosphorodiamidite in the presence of diisopropyl ammonium tetrazolide as activator in anhydrous CH2Cl2 to afford 8a,b in 86% and 81% yield, respectively (FIG. 1).
The synthesis of intercalating nucleic acid monomers containing a 1H-phenanthro[9,10-d]imidazol-2-yl group can be found in Osman (Bioorganic & Medicinal Chemistry, 2008).

Example 3

Figure 2:
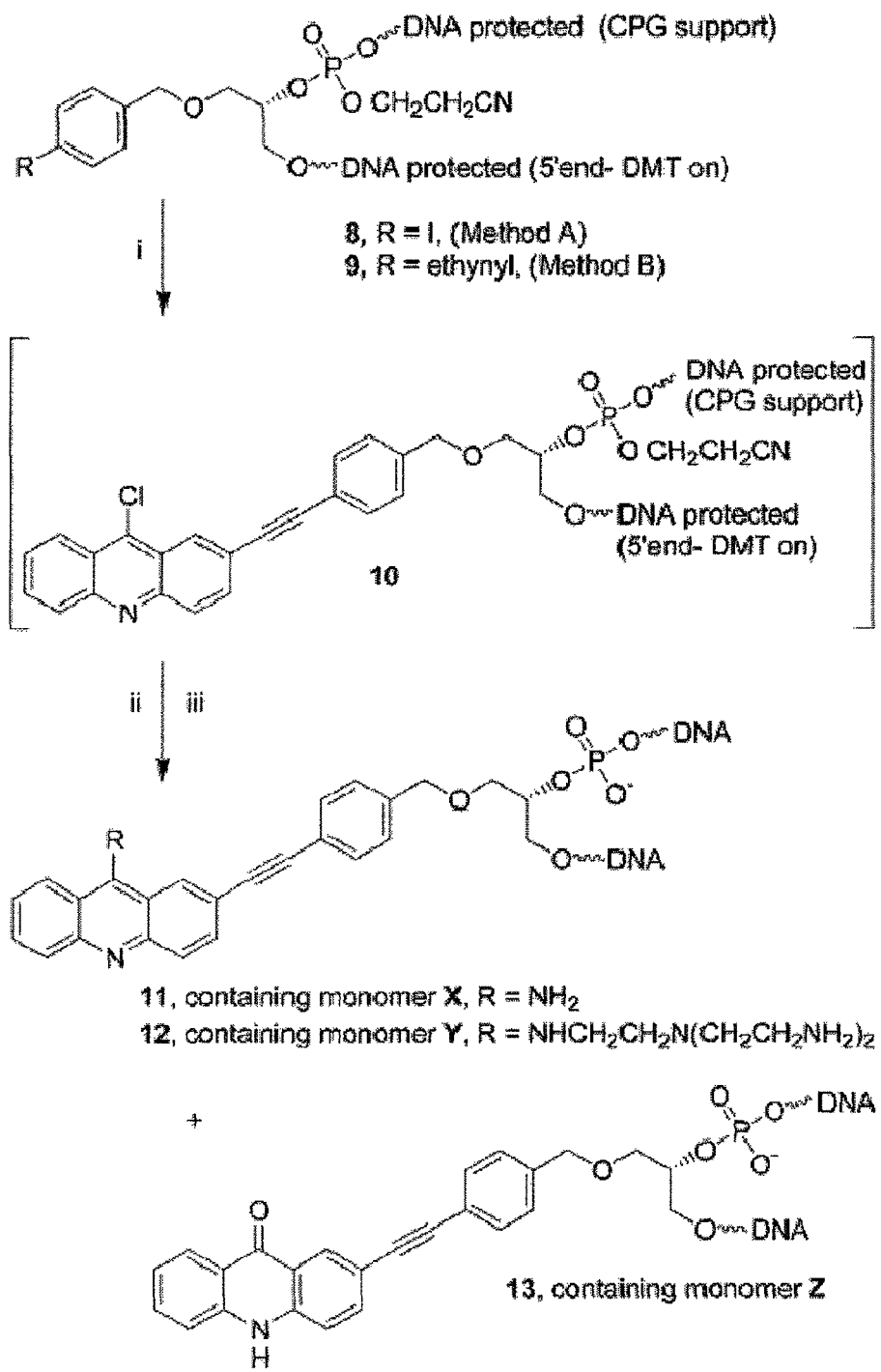
FIG. 2: The synthesis of intercalating nucleic acid monomer containing a Sonogahira type modification
(i) Reaction of 8 with 3 or reaction of 9 with 2 both using Pd(PPh3)4, CuI, DMF/Et$_3$N, Ar. (ii) 32% NH$_4$OH or 50% ethanolic solution of tris(2-aminoethyl)amine, room temperature for 2 h then 55° C. overnight. (iii) RP-HPLC; 80% aq AcOH, 3 M aq AcONa, 99% EtOH.

Synthesis of Intercalating Nucleic Acid Monomer Containing a Sonogahira Type Modification For the postsynthetic Sonogashira type modification on a solid phase, ONs with an insertion of (R)-1-O-(4-iodobenzyl) glycerol (8) or (R)-1-O-(4-ethynylbenzyl)glycerol (9) in the middle and at the 5'-end were used. CPG supports with DMT-on ONs 8 or 9 were treated with a freshly prepared Sonogashira coupling reagent mixture possessing ethynylacridine 3 or iodoacridine 2, respectively (FIG. 2). In both cases, the same product 10 on a solid support was obtained. However, Method B is preferred because the preparation of compound 9 is easy. It has previously been determined that double treatment of the CPG-bound oligonucleotides with a freshly prepared Sonogashira mixture increased the coupling efficiency.
The synthesis of intercalating nucleic acid monomer containing a Sonogahira type modification is discussed in Gèci et al. (Bioconjugate Chem, 2006).

Example 4

Figure 3:
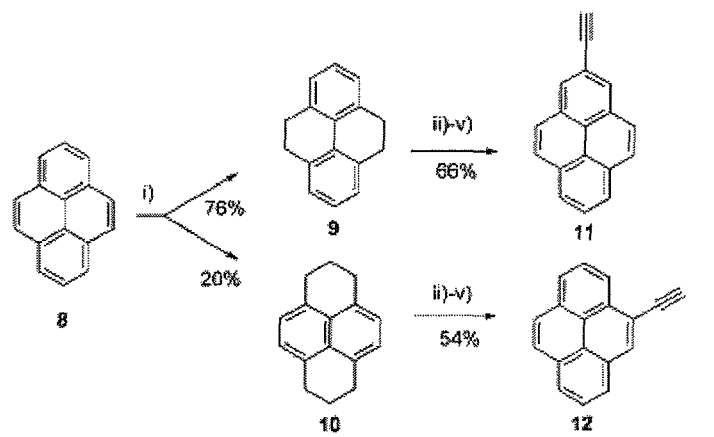
FIG. 3: The synthesis of 2- and 4-ethynylpyrenes into the para- and ortho-positions of (R)-1-O-phenylmethylglycerol and their incorporation into oligonucleotides
Reagent and conditions for synthesis: i) H$_2$ (160 atm), 10% Pd/C, EtOAc, 60° C., 24 h; ii) Ac$_2$O$_2$, Alcl$_3$, Ch$_2$Cl$_2$, 5° C.; iii) 2,3-dichloro-5,6-dicyano-1,4-benzoquinone (DDQ), toluene, 110° C., 1 h; iv) DMF, POCL$_3$; v) KOH, dioxane, reflux, 2 h.
Figure 3:
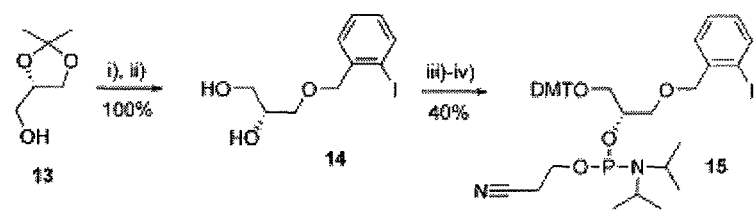

The Synthesis of 2- and 4-ethynylpyrenes and Their Incorporation Into Oligonucleotides 2- and 4-substituted pyrenes are not readily available owing to the fact that electrophilic substitution on pyrene (8 in FIG. 3) is directed to the electron-rich position 1. Pyrene derivatives substituted in position 2 and 4 can be prepared from 4,5,9,10-tetrahydropyrene (9) and 1,2,3,6,7,8-hexahydropyrene (10), respectively, by electrophilic substitution followed by aromatization. Although 10 is commercially available, it is rather expensive. Tetrahydropyrene (9) can be prepared by Pd/C hydrogenolysis of commercial pyrene that has to be purified by column chromatography on silica or have the sulphur removed over Raney nickel prior to the reaction. The hydrogenolysis of the pyrene that has had the sulphur removed by Raney nickel gives a mixture of 9 and 10 (FIG. 3). The mixture is easily separable by chromatography on aluminium oxide. Compounds 9 and 10 is converted into the corresponding 2-ethynylpyrene (11) and 4-ethynylpyrene (12) by using successive acetylation, aromatization, Vilsmeier-Haack-Arnold transformation, and Bodendorf fragmentation.
A more thorough discussion of the synthesis of 2- and 4-ethynylpyrenes into the para- and ortho-positions of (R)-1-O-phenylmethylglycerol and their incorporation into oligonucleotides can be found in Filichev et al. (Chem. Eur. J, 2008)

The invention claimed is:

1. A method comprising the steps of
   a. Providing a template nucleic acid
   b. Providing a first oligonucleotide primer
   c. Providing a polymerase
   d. Providing nucleotide triphosphates
   e. Mixing the components of steps a-d and providing conditions that allow the first oligonucleotide primer to anneal to the template
   wherein the first oligonucleotide is an oligonucleotide of a length between 5 and 60 nt. comprising a triplex forming monomer unit (TINA monomer) of the formula Z,
   wherein Z is described by the general structure:

$X\text{-}L\text{-}I_1\text{-}C\text{-}I_2$ wherein X is a backbone monomer unit that can be incorporated into the backbone of a oligonucleotide or a oligonucleotide analogue, or PNA, or PNA analogues, L is a linker, $I_1$ is a first intercalator comprising at least one flat conjugated system, C is an optional conjugator and $I_2$ is a second intercalator comprising at least one flat conjugated system
   f. Under conditions allowing primer extension, extending the first oligonucleotide annealed to the template.

2. The method of claim 1, wherein Z is located at the 5' end of the oligonucleotide.

3. The method of claim 1, wherein X is a backbone monomer unit of an oligonucleotide or an oligonucleotide analogue, or PNA, or PNA analogues, and wherein X comprises alkylenediol, L is a linker comprising an alkyl chain, an oxaalkyl chain, an azaalkyl chain, a thiaalkyl chain, carboxamide group, a thiocarboxamide group, a sulphonamide group or combinations thereof and comprises between 0-60, $I_1$ is a monocyclic or a polycyclic aromatic ringsystem selected from the group consisting of benzene, naphthalene, azulene and bicyclic heteroaromatic ring systems, $I_2$ is selected from the group of bicyclic aromatic ringsystems, tricyclic aromatic ringsystems, tetracyclic aromatic ringsystems, pentacyclic aromatic ringsystems and heteroaromatic analogues thereof and substitutions thereof.

4. The method of claim 1, wherein C is a conjugator selected from the group of alkyl of 1 to 12 carbons, alkenyl of from 2 to 12 carbons, alkynyl 2 to 25 carbons or diazo or combinations thereof with a length of no more than 25 carbons or/and nitrogen atoms.

5. The method of claim 1, wherein $I_1$ and $I_2$ is linked directly via a conjugated system.

6. The method of claim 1, wherein the Z can be described by the formula:

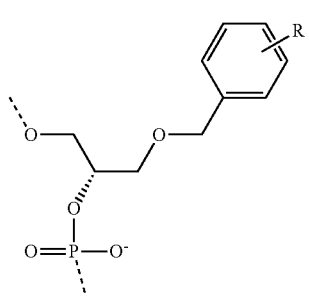

wherein R is selected from the group of arylethynyl.

7. The method of claim 1, wherein the oligonucleotide further comprises modified nucleotide monomer units selected from the group consisting of DNA units, RNA units, LNA units and 2'-OH-modified units.

8. The method of claim 1, wherein the 3' end of the oligonucleotide comprises a contiguous stretch of 3 deoxynucleotides.

9. The method of claim 1, wherein the oligonucleotide further comprises a restriction site.

10. The method of claim 1, wherein the oligonucleotide further comprises a fluorophor selected from the group consisting of FAM™, TET™, JOE™, VIC™, SYBR® Green; 6 FAM, HEX, TET, TAMRA, JOE, ROX, Fluorescein, Cy3, Cy5, Cy5.5, Texas Red, Rhodamine, Rhodamine Green, Rhodamine Red, 6-CarboxyRhodamine 6G, Oregon Green 488, Alexa Flour, Oregon Green 500 or Oregon Green 514.

11. The method of claim 1, wherein the oligonucleotide further comprises a quenching dye selected from the group consisting of TAMRA™; Black Hole Quencher™, DABCYL, BHQ-1, BHQ-2, DDQ I, DDQ II and Eclipse Dark Quencher.

12. The method of claim 1, wherein the oligonucleotide or the nucleotide triphosphates are fluorescently labeled.

13. The method of claim 1, wherein a fraction of the nucleotide triphosphates are dideoxynucleotide triphosphates.

14. The method of claim 1, further comprising the steps of
g. Providing a second oligonucleotide primer, which is complementary to the first extension product of step f
h. Denaturing the product of the step f
i. Under conditions allowing primer extension, extending the second oligonucleotide primer annealed to the first extension product yielding a second extension product.

15. The method of claim 14, wherein the second oligonucleotide is an oligonucleotide comprising a TINA monomer of formula Z, wherein Z is described by the general structure: $X-L-I_1-C-I_2$, wherein X is a backbone monomer unit that can be incorporated into the backbone of a oligonucleotide or a oligonucleotide analogue, or PNA, or PNA analogues, L is a linker, $I_1$ is a first intercalator comprising at least one flat conjugated system, C is an optional conjugator and $I_2$ is a second intercalator comprising at least one flat conjugated system.

16. The method of claim 14, comprising at least 10 repetitions of denaturation, annealing and extension.

17. The method of claim 1, wherein the polymerase is thermo stable.

18. The method of claim 14, wherein the first or the second oligonucleotide comprises an RNA promoter sequence that enables transcription mediated amplification.

19. The method of claim 14, wherein the reaction mixture further comprises a first detection probe, comprising a sequence which is complementary to a region between the first and the second oligonucleotide primer binding site of the first or the second extension product.

20. The method of claim 19, wherein the probe is capable of forming a stem-loop structure.

21. The method of claim 19, wherein the reaction mixture further comprises a second detection probe that is complementary to a region between the first and the second oligonucleotide primer binding site of the first or the second extension product, and wherein the first and the second probe will base pair to adjacent sites, thereby bringing the 3' end of one probe into proximity with the 5' end of the other probe.

22. The method of claim 1, wherein the reaction mixture further comprises double stranded specific reporter dyes such as SYBR green I, SYBR green II and SYBR Gold.

23. The method of claim 21, wherein the reaction mixture further comprises a first triplex forming probe that can form a triplex with the double-stranded second extension product.

24. The method of claim 23, wherein the triplex forming probe is capable of forming a stem-loop structure.

25. The method of claim 23, wherein the reaction mixture comprises a second triplex forming probe, which form a triplex adjacent to the triplex formed with the first triplex probe.

26. The method of claim 25, wherein the first and the second triplex forming probe is joined by a linker.

27. The method of claim 25, wherein the first and/or the second triplex forming probe is an oligonucleotide comprising a TINA monomer of formula Z, wherein Z is described by the general structure: $X-L-I_1-C-I_2$, wherein X is a backbone monomer unit that can be incorporated into the backbone of a oligonucleotide or a oligonucleotide analogue, or PNA, or PNA analogues, L is a linker, $I_1$ is a first intercalator comprising at least one flat conjugated system, C is an optional conjugator and $I_2$ is a second intercalator comprising at least one flat conjugated system.

28. The method of claim 25, wherein first and/or the second the triplex forming probe comprises a contiguous stretch of at least 3 pyrimidines.

29. The method of claim 25, wherein the first and/or the second triplex forming probe comprises a contiguous stretch of at least 3 purines.

30. The method of claim 14, wherein the reaction further comprises a triplex forming oligonucleotide that can form a triplex with the first oligonucleotide annealed to a template strand or a with the second oligonucleotide annealed to a template strand, thereby stabilizing binding of the oligonucleotide to the template strand.

31. The method of claim 23, wherein the method comprises a third and a fourth oligonucleotide and also a restriction enzyme that enables isothermal strand displacement amplification reaction.

* * * * *

UNITED STATES PATENT AND TRADEMARK OFFICE
CERTIFICATE OF CORRECTION

PATENT NO. : 8,501,441 B2
APPLICATION NO. : 12/921561
DATED : August 6, 2013
INVENTOR(S) : Gorm Lisby It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 361 days.

Signed and Sealed this
Fifteenth Day of September, 2015

Michelle K. Lee
*Director of the United States Patent and Trademark Office*

SEQUENCE LISTING

<160> NUMBER OF SEQ ID NOS: 8

<210> SEQ ID NO 1
<211> LENGTH: 22
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 1
gggcgaatca cagattgaat ct                                              22

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcggttccaa acgtaccaa                                                  19

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gggcgaatca cagattgagt ct                                              22

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcggttccaa acgtatcaa                                                  19

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: TINA monomer

<400> SEQUENCE: 5
ngggcgaatc acagattgaa tct                                             23

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: TINA monomer

<400> SEQUENCE: 6
ngcggttcca aacgtaccaa                                                 20
```

```
<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: TINA monomer

<400> SEQUENCE: 7
ngggcgaatc acagattgag tct                                              23

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: TINA monomer

<400> SEQUENCE: 8
ngcggttcca aacgtatcaa                                                  20
```